(12) United States Patent
Walton et al.

(10) Patent No.: US 11,344,663 B2
(45) Date of Patent: May 31, 2022

(54) SUCTION DEVICE AND DRESSING

(71) Applicant: T.J.Smith and Nephew, Limited, Hull (GB)

(72) Inventors: Edward William Walton, Burnley (GB); George Russell Walton, Ivyland, PA (US)

(73) Assignee: T.J.Smith and Nephew, Limited, Hull (GB)

( * ) Notice: Subject to any disclaimer, the term of this patent is extended or adjusted under 35 U.S.C. 154(b) by 797 days.

(21) Appl. No.: 16/201,508

(22) Filed: Nov. 27, 2018

(65) Prior Publication Data

US 2019/0167865 A1 Jun. 6, 2019

Related U.S. Application Data

(63) Continuation of application No. 15/366,999, filed on Dec. 1, 2016, now Pat. No. 10,143,784, which is a continuation of application No. 14/447,423, filed on Jul. 30, 2014, now abandoned, which is a continuation of application No. 12/744,302, filed as
(Continued)

(51) Int. Cl.
| | |
|---|---|
| *A61M 1/00* | (2006.01) |
| *A61M 13/00* | (2006.01) |
| *A61F 13/00* | (2006.01) |

(52) U.S. Cl.
CPC ......... *A61M 1/86* (2021.05); *A61F 13/00068* (2013.01); *A61M 1/0023* (2013.01); *A61M 1/74* (2021.05); *A61M 1/80* (2021.05); *A61M 1/81* (2021.05); *A61M 1/90* (2021.05); *A61M 1/962* (2021.05); *A61F 2013/0028* (2013.01)

(58) Field of Classification Search
CPC combination set(s) only.
See application file for complete search history.

(56) References Cited

U.S. PATENT DOCUMENTS

| 2,318,888 A | 5/1943 | Sanders |
| 2,682,873 A | 7/1954 | Evans et al. |
| 3,115,138 A | 12/1963 | McElvenny et al. |
| (Continued) | | |

FOREIGN PATENT DOCUMENTS

| CA | 2 349 638 | 5/2000 |
| DE | 34 43 101 | 5/1986 |
| (Continued) | | |

OTHER PUBLICATIONS

"Technology Watch", May 1989, in 1 page.
(Continued)

*Primary Examiner* — Guy K Townsend
(74) *Attorney, Agent, or Firm* — Knobbe, Martens, Olson & Bear, LLP

(57) ABSTRACT

Some embodiments are directed to a system 10 for the application of topical negative pressure therapy to a site 18 on the body of a mammal. Some embodiments of the system 10 comprise a piston 22 and cylinder 24 device 12 having a self-contained power source for the generation of a reduced pressure and for aspirating the site 18. Some embodiments of the system 10 comprise a dressing 14 sealably surrounding the site 18 that can be operably connected to the device 12 by a conduit means 16 to apply the reduced pressure to the site 18.

11 Claims, 3 Drawing Sheets

Related U.S. Application Data application No. PCT/US2008/084433 on Nov. 21, 2008, now Pat. No. 8,808,259.

(60) Provisional application No. 60/989,723, filed on Nov. 21, 2007.

(56) References Cited

U.S. PATENT DOCUMENTS

| | | |
|---|---|---|
| 3,286,711 A | 11/1966 | MacLeod |
| 3,315,665 A | 4/1967 | MacLeod |
| 3,841,331 A | 10/1974 | Wilder et al. |
| 3,896,810 A | 7/1975 | Akiyama |
| 3,972,328 A | 8/1976 | Chen |
| 4,029,598 A | 6/1977 | Neisius et al. |
| 4,112,949 A * | 9/1978 | Rosenthal ............ A61M 1/0011 604/319 |
| 4,117,551 A | 9/1978 | Books et al. |
| 4,136,696 A | 1/1979 | Nehring |
| 4,316,466 A | 2/1982 | Babb |
| 4,404,924 A | 9/1983 | Goldbert et al. |
| 4,468,227 A | 8/1984 | Jensen |
| 4,529,402 A | 7/1985 | Weilbacher et al. |
| 4,538,920 A | 9/1985 | Drake et al. |
| 4,648,870 A | 3/1987 | Goldberg et al. |
| 4,713,052 A | 12/1987 | Beck et al. |
| 4,728,499 A | 3/1988 | Fehder |
| 4,753,536 A | 6/1988 | Spehar et al. |
| 4,767,026 A | 8/1988 | Keller |
| 4,771,919 A | 9/1988 | Ernst |
| 4,778,446 A | 10/1988 | Jensen |
| 4,795,428 A | 1/1989 | Hwang |
| 4,795,435 A | 1/1989 | Steer |
| 4,798,583 A | 1/1989 | Beck et al. |
| 4,813,942 A | 3/1989 | Alvarez |
| 4,872,450 A | 10/1989 | Austad |
| 4,930,997 A | 6/1990 | Bennett |
| 4,969,880 A | 11/1990 | Zamierowski |
| 4,979,944 A | 12/1990 | Luzsicza |
| 4,981,474 A | 1/1991 | Bopp et al. |
| 5,010,115 A | 4/1991 | Grisoni |
| 5,011,381 A | 4/1991 | Neward |
| 5,056,510 A | 10/1991 | Gilman |
| 5,064,653 A | 11/1991 | Sessions et al. |
| 5,071,409 A | 12/1991 | Rosenberg |
| 5,080,493 A | 1/1992 | McKown et al. |
| 5,152,757 A | 10/1992 | Eriksson |
| 5,176,663 A | 1/1993 | Svedman et al. |
| 5,181,905 A | 1/1993 | Flam |
| 5,238,732 A | 8/1993 | Krishnan |
| 5,249,709 A | 10/1993 | Duckworth et al. |
| 5,266,326 A | 11/1993 | Barry et al. |
| 5,333,760 A | 8/1994 | Simmen et al. |
| 5,445,604 A | 8/1995 | Lang |
| 5,456,745 A | 10/1995 | Rorefer et al. |
| 5,505,210 A | 4/1996 | Clement |
| 5,549,584 A | 8/1996 | Gross |
| 5,582,596 A | 12/1996 | Fukunaga et al. |
| 5,583,114 A | 12/1996 | Barrows et al. |
| 5,609,271 A | 3/1997 | Keller et al. |
| 5,612,050 A | 3/1997 | Rowe et al. |
| 5,636,643 A * | 6/1997 | Argenta ................ A61M 1/90 602/42 |
| 5,645,081 A | 7/1997 | Argenta et al. |
| 5,660,823 A | 8/1997 | Chakrabarti et al. |
| 5,662,924 A | 9/1997 | Rhodes |
| 5,697,920 A | 12/1997 | Gibbons |
| 5,707,499 A | 1/1998 | Joshi et al. |
| 5,713,881 A | 2/1998 | Rezai et al. |
| 5,717,030 A | 2/1998 | Dunn et al. |
| 5,747,064 A | 5/1998 | Burnett et al. |
| 5,759,570 A | 6/1998 | Arnold |
| 5,776,193 A | 7/1998 | Kwan et al. |
| 5,795,584 A | 8/1998 | Totakura et al. |
| 5,834,007 A | 11/1998 | Kubota |
| 5,852,126 A | 12/1998 | Barnard et al. |
| 5,874,500 A | 2/1999 | Rhee et al. |
| 5,928,265 A | 7/1999 | Fleischmann |
| 5,945,115 A | 8/1999 | Dunn et al. |
| 5,954,680 A | 9/1999 | Augustine |
| 5,962,010 A | 10/1999 | Greff et al. |
| 5,998,472 A | 12/1999 | Berger et al. |
| 6,010,527 A | 1/2000 | Augustine et al. |
| 6,048,337 A * | 4/2000 | Svedman ............ A61M 37/00 604/289 |
| 6,071,267 A | 6/2000 | Zamierowski |
| 6,110,197 A | 8/2000 | Augustine et al. |
| 6,142,982 A * | 11/2000 | Hunt ....................... A61M 1/80 604/313 |
| 6,143,352 A | 11/2000 | Clark et al. |
| 6,165,201 A | 12/2000 | Sawhney et al. |
| 6,168,788 B1 | 1/2001 | Wortham |
| 6,174,306 B1 | 1/2001 | Fleischmann |
| 6,214,332 B1 | 4/2001 | Askill et al. |
| 6,252,129 B1 | 6/2001 | Coffee |
| 6,254,567 B1 | 7/2001 | Treu et al. |
| 6,391,294 B1 | 5/2002 | Dettmar et al. |
| 6,398,761 B1 | 6/2002 | Bills et al. |
| 6,447,802 B2 | 9/2002 | Sessions et al. |
| 6,458,109 B1 * | 10/2002 | Henley ................ A61M 1/732 604/289 |
| 6,486,285 B2 | 11/2002 | Fujita |
| 6,495,127 B1 | 12/2002 | Wallace et al. |
| 6,509,031 B1 | 1/2003 | Miller et al. |
| 6,521,251 B2 | 2/2003 | Askill et al. |
| 6,547,467 B2 | 4/2003 | Quintero |
| 6,548,730 B1 | 4/2003 | Patel et al. |
| 6,575,940 B1 | 6/2003 | Levinson et al. |
| 6,596,704 B1 | 7/2003 | Court et al. |
| 6,626,891 B2 | 9/2003 | Ohmstede |
| 6,627,216 B2 | 9/2003 | Brandt et al. |
| 6,629,774 B1 | 10/2003 | Guruendeman |
| 6,685,681 B2 | 2/2004 | Lockwood et al. |
| 6,730,299 B1 | 5/2004 | Tayot et al. |
| 6,752,794 B2 | 6/2004 | Lockwood et al. |
| 6,764,462 B2 | 7/2004 | Risk, Jr. et al. |
| 6,790,438 B1 | 9/2004 | Constancis et al. |
| 6,824,533 B2 | 11/2004 | Risk, Jr. et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,070,584 B2 | 7/2006 | Johnson et al. |
| 7,108,683 B2 | 9/2006 | Zamierowski |
| 7,118,545 B2 | 10/2006 | Boyde |
| 7,128,735 B2 | 10/2006 | Weston |
| 7,129,210 B2 | 10/2006 | Lowinger et al. |
| 7,141,714 B2 | 11/2006 | Nielsen |
| 7,214,202 B1 | 5/2007 | Vogel et al. |
| 7,216,651 B2 | 5/2007 | Argenta et al. |
| 7,279,612 B1 | 10/2007 | Heaton et al. |
| 7,303,757 B2 | 12/2007 | Schankereli et al. |
| 7,361,184 B2 | 4/2008 | Joshi |
| 7,381,859 B2 | 6/2008 | Hunt et al. |
| 7,494,482 B2 | 2/2009 | Orgill et al. |
| 7,524,315 B2 | 4/2009 | Blott et al. |
| 7,534,927 B2 | 5/2009 | Lockwood |
| 7,553,306 B1 | 6/2009 | Hunt et al. |
| 7,569,742 B2 | 8/2009 | Haggstrom et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,645,269 B2 | 1/2010 | Zamierowski |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,745,681 B1 | 6/2010 | Ferguson |
| 7,749,531 B2 | 7/2010 | Booher |

(56) References Cited

U.S. PATENT DOCUMENTS

| | | |
|---|---|---|
| 7,753,894 B2 | 7/2010 | Blott et al. |
| 7,754,937 B2 | 7/2010 | Boehringer et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,769 B2 | 7/2010 | Johnson et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,450 B2 | 9/2010 | Blott et al. |
| 7,803,980 B2 | 9/2010 | Griffiths et al. |
| 7,811,269 B2 | 10/2010 | Boynton et al. |
| 7,815,616 B2 | 10/2010 | Boehringer et al. |
| 7,828,782 B2 | 11/2010 | Suzuki |
| 7,838,717 B2 | 11/2010 | Haggstrom et al. |
| 7,846,141 B2 | 12/2010 | Weston |
| 7,862,831 B2 | 1/2011 | Wang et al. |
| 7,880,050 B2 | 2/2011 | Robinson et al. |
| 7,883,494 B2 | 2/2011 | Martin |
| 7,896,823 B2 | 3/2011 | Mangrum et al. |
| 7,909,805 B2 | 3/2011 | Weston |
| 7,910,135 B2 | 3/2011 | St. John et al. |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 7,976,519 B2 | 7/2011 | Bubb et al. |
| 8,007,164 B2 | 8/2011 | Miyano et al. |
| 8,007,257 B2 | 8/2011 | Heaton et al. |
| 8,007,481 B2 | 8/2011 | Schuessler et al. |
| 8,034,037 B2 | 10/2011 | Adams et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,097,272 B2 | 1/2012 | Addison |
| 8,105,295 B2 | 1/2012 | Blott et al. |
| 8,118,794 B2 | 2/2012 | Weston et al. |
| 8,119,160 B2 | 2/2012 | Looney et al. |
| 8,133,211 B2 | 3/2012 | Cavanaugh, II et al. |
| 8,152,785 B2 | 4/2012 | Vitaris |
| 8,158,844 B2 | 4/2012 | McNeil |
| 8,162,907 B2 | 4/2012 | Heagle |
| 8,162,909 B2 | 4/2012 | Blott et al. |
| 8,192,409 B2 | 6/2012 | Hardman et al. |
| 8,207,392 B2 | 6/2012 | Haggstrom et al. |
| 8,226,942 B2 | 7/2012 | Charier et al. |
| 8,235,955 B2 | 8/2012 | Blott et al. |
| 8,235,972 B2 | 8/2012 | Adahan |
| 8,241,261 B2 | 8/2012 | Randolph et al. |
| 8,246,606 B2 | 8/2012 | Stevenson et al. |
| 8,257,327 B2 | 9/2012 | Blott et al. |
| 8,273,368 B2 | 9/2012 | Ambrosio et al. |
| 8,282,611 B2 | 10/2012 | Weston |
| 8,303,552 B2 | 11/2012 | Weston |
| 8,308,714 B2 | 11/2012 | Weston et al. |
| 8,323,264 B2 | 12/2012 | Weston et al. |
| 8,338,402 B2 | 12/2012 | Fry et al. |
| 8,348,910 B2 | 1/2013 | Blott et al. |
| 8,366,692 B2 | 2/2013 | Weston |
| 8,372,049 B2 | 2/2013 | Jaeb et al. |
| 8,372,050 B2 | 2/2013 | Jaeb et al. |
| 8,382,731 B2 | 2/2013 | Johannison |
| 8,398,614 B2 | 3/2013 | Blott et al. |
| 8,409,157 B2 | 4/2013 | Haggstrom et al. |
| 8,410,189 B2 | 4/2013 | Carnahan et al. |
| 8,425,478 B2 | 4/2013 | Olson |
| 8,444,612 B2 | 5/2013 | Patel et al. |
| 8,460,255 B2 | 6/2013 | Joshi et al. |
| 8,529,548 B2 | 9/2013 | Blott et al. |
| 8,535,296 B2 | 9/2013 | Blott et al. |
| 8,545,464 B2 | 10/2013 | Weston |
| 8,545,466 B2 | 10/2013 | Andresen et al. |
| 8,628,505 B2 | 1/2014 | Weston |
| 8,641,691 B2 | 2/2014 | Fink |
| 8,663,198 B2 | 3/2014 | Buan et al. |
| 8,679,079 B2 | 3/2014 | Heaton et al. |
| 8,715,256 B2 | 5/2014 | Greener |
| 8,753,670 B2 | 6/2014 | Delmotte |
| 8,764,732 B2 | 7/2014 | Hartwell |
| 8,795,243 B2 | 8/2014 | Weston |
| 8,795,635 B2 | 8/2014 | Tamarkin et al. |
| 8,795,713 B2 | 8/2014 | Makower et al. |
| 8,808,259 B2 * | 8/2014 | Walton ............... A61M 1/74 604/319 |
| 8,808,274 B2 | 8/2014 | Hartwell |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,852,170 B2 | 10/2014 | Weston et al. |
| 8,945,030 B2 | 2/2015 | Weston |
| 8,956,336 B2 | 2/2015 | Haggstrom et al. |
| 8,968,773 B2 | 3/2015 | Thomas et al. |
| 9,012,714 B2 | 4/2015 | Fleischmann |
| 9,028,872 B2 | 5/2015 | Gaserod et al. |
| 9,044,579 B2 | 6/2015 | Blott et al. |
| 9,061,095 B2 | 6/2015 | Adie et al. |
| 9,168,330 B2 | 10/2015 | Joshi et al. |
| 9,199,012 B2 | 12/2015 | Vitaris et al. |
| 9,220,822 B2 | 12/2015 | Hartwell et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,387,126 B2 | 7/2016 | Blott et al. |
| 9,446,178 B2 | 9/2016 | Blott et al. |
| 9,452,248 B2 | 9/2016 | Blott et al. |
| 9,629,986 B2 | 4/2017 | Patel et al. |
| 9,669,138 B2 | 6/2017 | Joshi et al. |
| 9,795,725 B2 | 10/2017 | Joshi et al. |
| 9,844,473 B2 | 12/2017 | Blott et al. |
| 9,956,121 B2 | 5/2018 | Hartwell |
| 9,962,474 B2 | 5/2018 | Greener |
| 10,016,309 B2 | 7/2018 | Hartwell |
| 10,105,471 B2 | 10/2018 | Weston |
| 10,143,784 B2 * | 12/2018 | Walton ............... A61M 1/0023 |
| 2001/0004082 A1 | 6/2001 | Keller et al. |
| 2001/0034499 A1 | 10/2001 | Sessions et al. |
| 2001/0043913 A1 | 11/2001 | Spaans et al. |
| 2002/0038826 A1 | 4/2002 | Hurray et al. |
| 2002/0122771 A1 | 9/2002 | Holland et al. |
| 2002/0145007 A1 | 10/2002 | Sawhney et al. |
| 2002/0187182 A1 | 12/2002 | Kramer et al. |
| 2002/0198490 A1 | 12/2002 | Wirt et al. |
| 2003/0040478 A1 | 2/2003 | Drucker et al. |
| 2003/0069535 A1 | 4/2003 | Shalaby |
| 2003/0125646 A1 | 7/2003 | Whitlock |
| 2003/0143189 A1 | 7/2003 | Askill et al. |
| 2003/0183653 A1 | 10/2003 | Bills |
| 2004/0033466 A1 | 2/2004 | Shellard et al. |
| 2004/0037897 A1 | 2/2004 | Benjamin et al. |
| 2004/0049187 A1 | 3/2004 | Burnett et al. |
| 2004/0057855 A1 | 3/2004 | Gerlach et al. |
| 2004/0064132 A1 * | 4/2004 | Boehringer ........ A61M 1/0011 602/43 |
| 2004/0073152 A1 | 4/2004 | Karason et al. |
| 2004/0127836 A1 | 7/2004 | Sigurjonsson et al. |
| 2004/0167617 A1 | 8/2004 | Voellmicke et al. |
| 2004/0171998 A1 | 9/2004 | Marasco, Jr. |
| 2005/0058694 A1 * | 3/2005 | Nielsen ............... A61L 15/28 424/445 |
| 2005/0070835 A1 * | 3/2005 | Joshi ............... A61M 1/962 602/41 |
| 2005/0222527 A1 * | 10/2005 | Miller ............... A61M 27/00 602/1 |
| 2005/0222528 A1 * | 10/2005 | Weston ............... A61M 1/90 602/1 |
| 2005/0230422 A1 | 10/2005 | Muller et al. |
| 2005/0261642 A1 * | 11/2005 | Weston ............... A61M 1/90 604/313 |
| 2006/0009744 A1 | 1/2006 | Erdman et al. |

(56) References Cited

U.S. PATENT DOCUMENTS

| | | | |
|---|---|---|---|
| 2006/0052839 A1 | 3/2006 | Kim et al. | |
| 2006/0079599 A1 | 4/2006 | Arthur | |
| 2006/0155260 A1* | 7/2006 | Blott | A61M 27/00 604/543 |
| 2006/0173514 A1* | 8/2006 | Biel | A61K 9/703 607/88 |
| 2006/0253082 A1 | 11/2006 | Mcintosh et al. | |
| 2006/0273109 A1 | 12/2006 | Keller | |
| 2007/0004896 A1 | 1/2007 | Ito et al. | |
| 2007/0009580 A1 | 1/2007 | DiCosmo et al. | |
| 2007/0027414 A1 | 2/2007 | Hoffman et al. | |
| 2007/0032762 A1 | 2/2007 | Vogel | |
| 2007/0040454 A1 | 2/2007 | Freudenberger et al. | |
| 2007/0055209 A1 | 3/2007 | Patel et al. | |
| 2007/0129707 A1* | 6/2007 | Blott | A61M 1/0058 604/308 |
| 2007/0141101 A1 | 6/2007 | Nugent et al. | |
| 2007/0147947 A1 | 6/2007 | Stenton et al. | |
| 2007/0164047 A1 | 7/2007 | Reidt et al. | |
| 2007/0167926 A1* | 7/2007 | Blott | A61M 3/0229 604/304 |
| 2007/0185463 A1 | 8/2007 | Mulligan | |
| 2007/0203062 A1 | 8/2007 | Ellis-Behnke et al. | |
| 2007/0219532 A1 | 9/2007 | Karpowicz et al. | |
| 2007/0225663 A1 | 9/2007 | Watt et al. | |
| 2007/0265586 A1* | 11/2007 | Joshi | A61L 15/425 604/313 |
| 2007/0276195 A1 | 11/2007 | Xu et al. | |
| 2007/0276309 A1 | 11/2007 | Xu et al. | |
| 2008/0004549 A1 | 1/2008 | Anderson et al. | |
| 2008/0031748 A1 | 2/2008 | Ihle et al. | |
| 2008/0060550 A1 | 3/2008 | MacDonald et al. | |
| 2008/0065001 A1 | 3/2008 | DiNucci et al. | |
| 2008/0071216 A1 | 3/2008 | Locke et al. | |
| 2008/0089173 A1 | 4/2008 | Lu et al. | |
| 2008/0091133 A1 | 4/2008 | Matter | |
| 2008/0132821 A1 | 6/2008 | Propp et al. | |
| 2008/0139674 A1 | 6/2008 | Archambeau et al. | |
| 2008/0206155 A1 | 8/2008 | Tamarkin et al. | |
| 2008/0208163 A1 | 8/2008 | Wilkie | |
| 2008/0254103 A1 | 10/2008 | Harris et al. | |
| 2008/0287880 A1 | 11/2008 | Keller | |
| 2008/0294127 A1* | 11/2008 | Blott | A61H 9/0057 604/305 |
| 2008/0300555 A1* | 12/2008 | Olson | A61F 13/00068 604/313 |
| 2008/0306456 A1 | 12/2008 | Riesinger | |
| 2008/0314929 A1 | 12/2008 | Keller | |
| 2009/0012482 A1 | 1/2009 | Pinto | |
| 2009/0020561 A1 | 1/2009 | Keller | |
| 2009/0022779 A1 | 1/2009 | Kelly et al. | |
| 2009/0030086 A1 | 1/2009 | Eady et al. | |
| 2009/0054855 A1 | 2/2009 | Blott et al. | |
| 2009/0054856 A1 | 2/2009 | Mormino et al. | |
| 2009/0093550 A1 | 4/2009 | Rolfes et al. | |
| 2009/0098073 A1 | 4/2009 | MacDonald et al. | |
| 2009/0105671 A1 | 4/2009 | Daggar et al. | |
| 2009/0125004 A1 | 5/2009 | Shen et al. | |
| 2009/0134186 A1 | 5/2009 | Keller | |
| 2009/0157017 A1 | 6/2009 | Ambrosio | |
| 2009/0157024 A1 | 6/2009 | Song | |
| 2009/0196844 A1 | 8/2009 | Choi et al. | |
| 2009/0221977 A1 | 9/2009 | Blott et al. | |
| 2009/0234306 A1 | 9/2009 | Vitaris | |
| 2009/0275872 A1 | 11/2009 | Addison et al. | |
| 2009/0299251 A1 | 12/2009 | Buan | |
| 2009/0299255 A1 | 12/2009 | Kazala, Jr. et al. | |
| 2009/0299306 A1 | 12/2009 | Buan | |
| 2009/0312723 A1 | 12/2009 | Blott et al. | |
| 2010/0022972 A1 | 1/2010 | Lina et al. | |
| 2010/0030132 A1 | 2/2010 | Niezgoda et al. | |
| 2010/0036305 A1 | 2/2010 | Green | |
| 2010/0036334 A1* | 2/2010 | Heagle | A61F 13/0216 604/319 |
| 2010/0042074 A1* | 2/2010 | Weston | A61M 1/81 604/543 |
| 2010/0069829 A1 | 3/2010 | Hutchinson et al. | |
| 2010/0069850 A1 | 3/2010 | Fabo | |
| 2010/0069858 A1 | 3/2010 | Olson | |
| 2010/0094234 A1 | 4/2010 | Ramella et al. | |
| 2010/0106112 A1 | 4/2010 | Vogel | |
| 2010/0106117 A1* | 4/2010 | Lockwood | A61F 13/00068 604/319 |
| 2010/0122417 A1 | 5/2010 | Vrzalik et al. | |
| 2010/0125258 A1 | 5/2010 | Coulthard et al. | |
| 2010/0191196 A1* | 7/2010 | Heagle | B29C 66/81433 604/313 |
| 2010/0210986 A1 | 8/2010 | Sanders | |
| 2010/0230467 A1 | 9/2010 | Crisuolo et al. | |
| 2010/0249733 A9 | 9/2010 | Blott et al. | |
| 2010/0262090 A1 | 10/2010 | Riesinger | |
| 2010/0262091 A1 | 10/2010 | Larsson | |
| 2010/0262094 A1* | 10/2010 | Walton | A61M 1/0023 604/319 |
| 2010/0280469 A1* | 11/2010 | Hall | A61M 1/90 604/319 |
| 2010/0305526 A1 | 12/2010 | Robinson et al. | |
| 2011/0021431 A1 | 1/2011 | Jones et al. | |
| 2011/0028919 A1* | 2/2011 | Johnnison | A61F 13/00068 604/319 |
| 2011/0033503 A1 | 2/2011 | Sinko et al. | |
| 2011/0086077 A1 | 4/2011 | McCrea et al. | |
| 2011/0118683 A1 | 5/2011 | Weston | |
| 2011/0257572 A1* | 10/2011 | Locke | A61M 1/0001 604/319 |
| 2011/0282309 A1* | 11/2011 | Adie | A61M 1/90 604/319 |
| 2012/0130332 A1 | 5/2012 | Cotton et al. | |
| 2012/0232502 A1* | 9/2012 | Lowing | A61F 13/00017 604/319 |
| 2012/0245540 A1* | 9/2012 | Zimnitsky | A61L 26/0066 424/618 |
| 2013/0053797 A1* | 2/2013 | Locke | A61M 1/86 604/319 |
| 2013/0096518 A1* | 4/2013 | Hall | A61M 1/90 604/319 |
| 2013/0138054 A1 | 5/2013 | Fleischmann | |
| 2013/0150814 A1 | 6/2013 | Buan | |
| 2013/0317406 A1* | 11/2013 | Locke | A61F 13/0259 604/358 |
| 2013/0338614 A1 | 12/2013 | Heaton et al. | |
| 2014/0031771 A1* | 1/2014 | Locke | A61M 1/732 156/60 |
| 2014/0163490 A1* | 6/2014 | Locke | A61M 1/964 604/319 |
| 2014/0228786 A1* | 8/2014 | Croizat | A61F 13/53 604/319 |
| 2014/0249495 A1* | 9/2014 | Mumby | A61F 13/00029 604/385.01 |
| 2014/0276490 A1* | 9/2014 | Locke | A61L 15/58 604/319 |
| 2014/0276491 A1* | 9/2014 | Luckemeyer | A61F 13/00068 604/319 |
| 2014/0316359 A1* | 10/2014 | Collinson | A61F 13/0209 604/319 |
| 2014/0358097 A1 | 12/2014 | Walton et al. | |
| 2015/0065965 A1 | 3/2015 | Haggstrom et al. | |
| 2015/0119830 A1* | 4/2015 | Luckemeyer | A61F 13/00051 604/319 |
| 2015/0119832 A1* | 4/2015 | Locke | A61F 13/0216 604/319 |
| 2015/0141941 A1* | 5/2015 | Allen | A61M 1/79 604/319 |
| 2015/0174304 A1* | 6/2015 | Askem | A61F 13/0246 604/319 |
| 2016/0175156 A1* | 6/2016 | Locke | A61F 13/0216 604/319 |
| 2016/0317357 A1 | 11/2016 | Vitaris et al. | |
| 2017/0007753 A1 | 1/2017 | Blott et al. | |
| 2017/0128642 A1 | 5/2017 | Buan | |
| 2017/0181896 A1 | 6/2017 | Hartwell | |

(56) References Cited

U.S. PATENT DOCUMENTS

| | | |
|---|---|---|
| 2017/0181897 A1 | 6/2017 | Hartwell |
| 2017/0252496 A1 | 9/2017 | Blott et al. |
| 2018/0064581 A1* | 3/2018 | Lowing ............ A61F 13/00012 |
| 2019/0091383 A1 | 3/2019 | Weston |

FOREIGN PATENT DOCUMENTS

| | | |
|---|---|---|
| DE | 3 935 818 | 5/1991 |
| DE | 20 2004 017 052 | 7/2005 |
| DE | 20 2005 019 670 | 4/2006 |
| EP | 0 340 018 | 11/1989 |
| EP | 0 521 434 | 1/1993 |
| EP | 0 858 810 | 8/1998 |
| EP | 0 888 141 | 1/1999 |
| EP | 1 007 015 | 6/2000 |
| EP | 1 029 585 | 8/2000 |
| EP | 1 105 171 | 6/2001 |
| EP | 1 105 180 | 6/2001 |
| EP | 1 107 813 | 6/2001 |
| EP | 1 030 657 | 10/2001 |
| EP | 1 306 123 | 5/2003 |
| EP | 1 440 737 | 7/2004 |
| EP | 1 923 077 | 11/2006 |
| EP | 1 476 217 | 3/2008 |
| EP | 1 955 887 | 8/2008 |
| EP | 2 111 804 | 10/2009 |
| EP | 2 218 431 | 8/2010 |
| EP | 2 462 908 | 6/2012 |
| FR | 1 163 907 | 10/1958 |
| GB | 1255395 | 12/1971 |
| GB | 2047438 | 11/1980 |
| GB | 2288734 | 11/1995 |
| GB | 2424582 | 10/2006 |
| GB | 2435419 | 2/2007 |
| WO | WO 1983/00742 | 3/1983 |
| WO | WO 1992/009301 | 6/1992 |
| WO | WO 1992/09651 | 6/1992 |
| WO | WO 1993/06802 | 4/1993 |
| WO | WO 1993/09176 | 5/1993 |
| WO | WO 1994/020133 | 9/1994 |
| WO | WO-9605873 A1 | 2/1996 |
| WO | WO 1996/40174 | 12/1996 |
| WO | WO 1997/03717 | 2/1997 |
| WO | WO 1997/33922 | 9/1997 |
| WO | WO 1997/42986 | 11/1997 |
| WO | WO 1998/03267 | 1/1998 |
| WO | WO 1998/06444 | 2/1998 |
| WO | WO 1998/046178 | 10/1998 |
| WO | WO 1999/17698 | 4/1999 |
| WO | WO 1999/30629 | 6/1999 |
| WO | WO 1999/047097 | 9/1999 |
| WO | WO 1999/65536 | 12/1999 |
| WO | WO 2000/38752 | 7/2000 |
| WO | WO 2000/61206 | 10/2000 |
| WO | WO 2000/62827 | 10/2000 |
| WO | WO 2000/064396 | 11/2000 |
| WO | WO 2001/062312 | 8/2001 |
| WO | WO 2001/066017 | 9/2001 |
| WO | WO 2001/093793 | 12/2001 |
| WO | WO 2002/02079 | 1/2002 |
| WO | WO 2002/070040 | 9/2002 |
| WO | WO 2002/083046 | 10/2002 |
| WO | WO 2002/094256 | 11/2002 |
| WO | WO 2002/102864 | 12/2002 |
| WO | WO 2003/030966 | 4/2003 |
| WO | WO 2003/074100 | 9/2003 |
| WO | WO 2004/037334 | 5/2004 |
| WO | WO 2004/054632 | 7/2004 |
| WO | WO 2004/077387 | 9/2004 |
| WO | WO 2005/017000 | 2/2005 |
| WO | WO 2005/018695 | 3/2005 |
| WO | WO 2005/025447 | 3/2005 |
| WO | WO 2005/046761 | 5/2005 |
| WO | WO 2005/046762 | 5/2005 |
| WO | WO 2005/051461 | 6/2005 |
| WO | WO 2005/105174 | 11/2005 |
| WO | WO 2005/105175 | 11/2005 |
| WO | WO 2005/105176 | 11/2005 |
| WO | WO 2005/118011 | 12/2005 |
| WO | WO 2005/123170 | 12/2005 |
| WO | WO 2006/014534 | 2/2006 |
| WO | WO 2006/030054 | 3/2006 |
| WO | WO 2006/034128 | 3/2006 |
| WO | WO 2006/046060 | 5/2006 |
| WO | WO 2006/052839 | 5/2006 |
| WO | WO 2006/135506 | 12/2006 |
| WO | WO 2007/030599 | 3/2007 |
| WO | WO 2007/030601 | 3/2007 |
| WO | WO 2007/041642 | 4/2007 |
| WO | WO 2007/062024 | 5/2007 |
| WO | WO 2007/067685 | 6/2007 |
| WO | WO 2007/070570 | 6/2007 |
| WO | WO 2007/084792 | 7/2007 |
| WO | WO 2007/085396 | 8/2007 |
| WO | WO 2007/087809 | 8/2007 |
| WO | WO 2007/088530 | 8/2007 |
| WO | WO 2007/106594 | 9/2007 |
| WO | WO 2007/124198 | 11/2007 |
| WO | WO 2008/036345 | 3/2008 |
| WO | WO 2008/039223 | 4/2008 |
| WO | WO 2008/076407 | 6/2008 |
| WO | WO 2008/082444 | 7/2008 |
| WO | WO 2008/112304 | 9/2008 |
| WO | WO 2008/134544 | 11/2008 |
| WO | WO 2008/134774 | 11/2008 |
| WO | WO 2008/135997 | 11/2008 |
| WO | WO 2008/141228 | 11/2008 |
| WO | WO 2008/141470 | 11/2008 |
| WO | WO 2009/019227 | 2/2009 |
| WO | WO 2009/019229 | 2/2009 |
| WO | WO 2009/034322 | 3/2009 |
| WO | WO 2009/042514 | 4/2009 |
| WO | WO 2009/047524 | 4/2009 |
| WO | WO 2009/052193 | 4/2009 |
| WO | WO 2009/060327 | 5/2009 |
| WO | WO 2009/062327 | 5/2009 |
| WO | WO 2009/066105 | 5/2009 |
| WO | WO 2009/070905 | 6/2009 |
| WO | WO 2009/077722 | 6/2009 |
| WO | WO 2009/078790 | 6/2009 |
| WO | WO 2009/088926 | 7/2009 |
| WO | WO 2009/103031 | 8/2009 |
| WO | WO 2009/124100 | 10/2009 |
| WO | WO 2009/126833 | 10/2009 |
| WO | WO 2009/145703 | 12/2009 |
| WO | WO 2009/146441 | 12/2009 |
| WO | WO 2009/158128 | 12/2009 |
| WO | WO 2010/006182 | 1/2010 |
| WO | WO 2010/033271 | 3/2010 |
| WO | WO 2010/051068 | 5/2010 |
| WO | WO 2010/059712 | 5/2010 |
| WO | WO 2010/142959 | 12/2010 |
| WO | WO 2010/147533 | 12/2010 |

OTHER PUBLICATIONS

Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

Kendall ULTEC Hydrocolloid Dressing (4"×4"), product ordering page, web page downloaded Jul. 13, 2014, in 1 page.

Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.

Protz, K., "Moderne Wundauflagen unterstutzen Heilungsprozess", Wundversorgung: Indikation und Anwendung, Geriatrie Journal, Apr. 2005, pp. 3333-3339, with translation, in 17 pages.

Smith & Nephew, "PICO Single Use Negative Pressure Wound Therapy System", spiral booklet, Mar. 2011, in 7 pages.

U.S. Appl. No. 60/852,369, filed Oct. 17, 2006, Weston et al.

(56) References Cited

OTHER PUBLICATIONS

Bevan, D. et al., "Diverse and potent activities of HGF/SF in skin wound repair", Journal of Pathology, vol. 203, 2004, pp. 831-838, in 8 pages.
Greer, S. et al., "Techniques for Applying Subatmospheric Pressure Dressing to Wounds in Difficult Regions of Anatomy", JWOCN, vol. 26(5), 1999, pp. 250-253, in 4 pages.
Info V.A.C. User Manual—KCI—Dec. 2006, in 76 pages.
Invitation to Pay Additional Fees and Partial Search Report, re PCT Application No. PCT/US2008/084433, dated Jul. 16, 2009.
International Search Report, re PCT Application No. PCT/US2008/084433, dated Oct. 15, 2009.
International Preliminary Reporton Patentability, re PCT Application No. PCT/US2008/084433, dated May 25, 2010.
Landis, E.M. et al., The Effects of Alternate Suction and Pressure on Blood Flow to the Lower Extremities, Alternate Suction and Pressure, J Clin Invest. Sep. 1933, vol. 12(5), pp. 925-961.
Mitchell, R. et al., "Role of Stem Cells in Tissue Homeostasis", Pocket Companion to Robbins and Cotran Pathologic Basis of Disease, 7th Edition, 2006, in 3 pages.
Morykwas, M. J. et al., "Nonsurgical Modalities to Enhance Healing and Care of Soft Tissue Wounds", Journal of the Southern Orthopaedic Association, vol. 6, No. 4, Winter 1997, in 12 pages.
Westaby, S. et al., "A Wound Irrigation Device", The Lancet, Sep. 2, 1978, pp. 503-504, in 2 pages.
Wound Suction, Nursing, Oct. 1975, USA pp. 52-53.

\* cited by examiner

SUCTION DEVICE AND DRESSING

PRIORITY INFORMATION

This application is a continuation of U.S. application Ser. No. 15/366,999, filed Dec. 1, 2016, which is a continuation of U.S. application Ser. No. 14/447,423, filed Jul. 30, 2014, which is a continuation of U.S. application Ser. No. 12/744,302, filed May 21, 2010, which is a U.S. National Phase of International Application No. PCT/US2008/084433, filed Nov. 21, 2008, designating the U.S. and published on May 28, 2009 as WO 2009/067711, which claims priority benefit under 35 U.S.C. § 119(e) of Provisional Application 60/989,723, filed Nov. 21, 2007 and titled SUCTION DEVICE AND DRESSING, which applications are hereby incorporated by reference as if fully set forth herein.

BACKGROUND

Field of the Invention

Some embodiments of the present application relate to treating a site on a body by applying reduced or negative pressure to the site.

Description of the Related Art

The treatment of open or chronic wounds that are too large to spontaneously close or otherwise fail to heal has long been a troublesome area of medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great causing excessive pressure to be exerted by the sutures upon the tissue adjacent to each suture. As a result, the adjacent tissue often becomes ischemic thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound may prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound may also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

There exist apparatuses utilizing reduced pressure for treatment of these types of wounds. However, the existing apparatuses do not have adequate means to provide access to the area of the wound beneath the cover or dressing without disturbing the seal (be it adhesive or otherwise) between the dressing and the healthy skin surrounding the wound. Additionally, use of the existing apparatuses is often limited to locally available power sources, or such apparatuses otherwise experience limitations in terms of the amount of suction that can be provided to the dressing in the absence of electrical power.

SUMMARY OF SOME EMBODIMENTS

Some embodiments set forth herein are directed to systems, methods and apparatuses for wound therapy. In particular, some embodiments disclosed herein relate to a system for the generation and application of reduced pressure (compared with ambient atmospheric pressure) to a site on a human or animal body and to a dressing (also referred to herein as a cover) at a wound site, and some embodiments relate to a wound dressing system configured to allow a user or medical practitioner to easily access a wound bed without disturbing a seal between the dressing and the healthy skin surrounding the wound. However, it will be appreciated that the systems, methods and apparatuses disclosed herein may have application to other fields. In certain preferred embodiments, the wounds being treated may include, but are not limited to, acute and chronic wounds, orthopedic trauma wounds, and post-Cesarean wounds, to name a few.

Some embodiments disclosed herein are directed to treating such wounds by a method for the application of topical negative pressure therapy to a site on the body of a mammal, the method comprising: providing a device comprising a cylinder, a piston disposed in the cylinder, and a power source operably connected to the piston, the power source being configured to exert a constant force on the piston; operably connecting the device to a dressing at the site by an aspirant conduit means, wherein the dressing can sealably surround the site; and applying a reduced pressure to the site. In some embodiments, the power source can be a self-contained mechanical motive power source such as, but not limited to, a resilient tension applying device. For example, without limitation the mechanical motive power source can be a coiled ribbon spring. The reduced pressure applied to the site can be held constant by the constant force exerted by the power source on the piston of the device. In some embodiments, the cylinder and piston can comprise a syringe type device, and the reduced pressure can be generated by actuating the piston of the device. Any of the configurations of the method for the application of topical negative pressure therapy to a site on the body of a mammal described above can further comprise operably connecting a mechanical pump (which can be a hand operated pump) to the dressing to generate the reduced pressure.

Some embodiments disclosed herein are directed to treating such wounds with a system for the application of topical negative pressure therapy to a site on the body of a mammal, the system comprising: a piston and cylinder device having a self-contained power source for the generation of a reduced pressure and for aspirating the site; and a dressing at the site operably connected to the device by an aspirant conduit or other conduit means to apply the reduced pressure to the site; wherein the dressing can sealably surround the site. In some embodiments, the device for the generation of reduced pressure can be a self-contained mechanical motive power source such as, but not limited to, a resilient tension applying device or other device that can apply a constant tension force. Some arrangements of the motive power source can have a coiled ribbon spring.

In any of the previously described embodiments, exudate from the site can be received by the piston and cylinder device, and/or the system can further be provided with a separate receptacle for receiving waste. Further, the piston and cylinder device can be a syringe-type device, and the device for the generation of reduced pressure can be a hand-held pump. Further, in any of the previously described embodiments, the dressing can comprise a first adherent base portion configured to sealably surround the site and a second detachable portion sealably and removably connectable to the first base portion. The first base portion and the second detachable portion of the dressing can have mutually engageable connection features which can, but are not required to, comprise male and female engaging portions and/or magnetic pieces such as magnetic tape or magnetic strips. Further, the second detachable portion can include an integral occlusive drape portion or membrane, and at least one of the first base portion, the second detachable portion, and the occlusive drape portion can be provided with a tubular spigot for the attachment of at least one separate aspirant conduit portion.

In some embodiments, any of the embodiments of the dressing described above can have a separate occlusive drape portion. Further, in any of the embodiments disclosed herein, either the first base portion or the second detachable portion, or both portions, can have an aspirant conduit incorporated therein. In some embodiments, the aspirant conduit can be incorporated with a separate occlusive drape portion. In any of the embodiments disclosed herein, the dressing or site can be provided with a wound filler and/or an absorbent material to absorb at least a portion of exudate from the site. The absorbent material can comprise, without limitation, polyacrylate particles. In some embodiments, the absorbent material can comprise carbomethoxycellulose.

Some embodiments disclosed herein are directed to a method of treating a wound comprising: sealably surrounding a wound site with a dressing having an adherent first base portion, and sealably connecting a second detachable portion to the first base portion. In some embodiments, the method can further comprise positioning an occlusive drape between the first and second base portions, while some embodiments of the second detachable portion can substantially completely cover the first base portion. Any of the embodiments of the methods of treating a wound described above can further comprise applying reduced pressure to the wound site.

In some embodiments, such wounds can be treated using an apparatus for the application of topical negative pressure therapy to a site on the skin of the body of a mammal, the apparatus comprising: a dressing configured to sealingly surround the site, the dressing comprising: a base portion configured to be supported by the skin surrounding the site, the base portion optionally comprising an aperture formed axially therethrough; a detachable portion removably supportable by the base portion; and a flexible membrane removably supportable by the base portion, the flexible membrane optionally being configured to at least cover the aperture formed in the base portion; wherein each of the base portion, the detachable portion, and the membrane are optionally formed from a substantially impermeably material; and the dressing can be configured to form an approximately hermetically sealed enclosure over the site when the detachable portion and the flexible membrane are supported by the base portion.

In some embodiments, the apparatus can further comprise a reduced pressure generation device (which can be, without limitation, a piston and cylinder device such as a syringe) configured to provide reduced pressure to the dressing, wherein the apparatus can be configured such that the reduced pressure generation, device is in fluid communication with the dressing. Additionally, the reduced pressure generation device can comprise a self-contained mechanical motive power source which can be, without limitation, a rolled spring. In some embodiments, the reduced pressure generation device can comprise a hand-held pump.

In some embodiments, such wounds can be treated using an apparatus for providing a source of reduced pressure to a cover, the apparatus comprising a conduit in communication with the cover; a first suction device configured to allow a user to reduce the pressure within the conduit, the first suction device being removably connectable to a valve member in communication with the conduit; a second suction device configured to allow a user to maintain the reduced pressure within the conduit, the second suction device being removably connectable to the valve member; and a power source configured to provide power to the second suction device.

In some embodiments, such wounds can be treated using a method for the application of topical negative pressure therapy to a site on the body of a mammal, the method comprising: operating a first source of negative or reduced pressure so as to provide reduced pressure to the cover; and disconnecting the first source of negative or reduced pressure from the cover without the loss of a substantial amount of reduced pressure in the cover.

In some embodiments, such wounds can be treated using a method for the application of topical negative pressure therapy to a site on the body of a mammal, the method comprising: sealingly enclosing the site with a cover so that ambient air is substantially prevented from entering a space between the cover and the site; connecting a suction device to the cover through a conduit so that the suction device is in fluid communication with the cover; operating the suction device until a desired level of reduced pressure within the dressing is achieved; connecting a mechanical vacuum system to the conduit so that the mechanical vacuum system is in fluid communication with the cover; providing a power source configured to provide power to the mechanical vacuum system; and operating the mechanical vacuum system so as to maintain a desired level of reduced pressure within the cover.

Some embodiments of the present disclosure are directed to a conduit insertion device for passing a length of conduit through a dressing (which can be, without limitation, any of the dressings disclosed herein), the conduit insertion device having a trocar supported within a length of conduit or tubing. In some embodiments, the conduit insertion device can be used to pass the conduit through either the flexible sheet or the second detachable portion of any of the embodiments of the dressing disclosed herein after the dressing has been positioned over the wound. Some arrangements of the conduit insertion device can be configured such that, after the conduit has been passed through the flexible sheet or the second detachable portion (if the flexible sheet is not use), a tabbed or flanged surface that can be formed on a portion of the conduit can be sealably adhered or otherwise attached to the outside surface of the flexible sheet or second detachable portion to secure the conduit thereto.

For example, in some embodiments, a trocar can be supported within the tubular length of conduit that can be inserted through the dressing such that the trocar protrudes past the distal end of the conduit. In this configuration, the trocar can be used to create a puncture hole in the flexible sheet, the second detachable portion of the dressing, and/or the base portion of the dressing to permit the tubing to pass therethrough. After the tubing has been passed therethrough, the conduit member may be advanced to a distance that is sufficient to permit an annular tabbed or flanged surface sealingly surrounding the tubing to be attached to, adhered to, or otherwise joined with the outside surface of the dressing so that an approximately hermetic seal is formed between the conduit member and the dressing, at which point the trocar may be withdrawn.

BRIEF DESCRIPTION OF THE DRAWINGS

These and other features, aspects and advantages will now be described in connection with certain embodiments, with reference to the accompanying drawings. The illustrated embodiments, however, are merely examples and are not intended to be limiting. The following are brief descriptions of the drawings.

DETAILED DESCRIPTION OF THE PREFERRED EMBODIMENT

Figure 1:
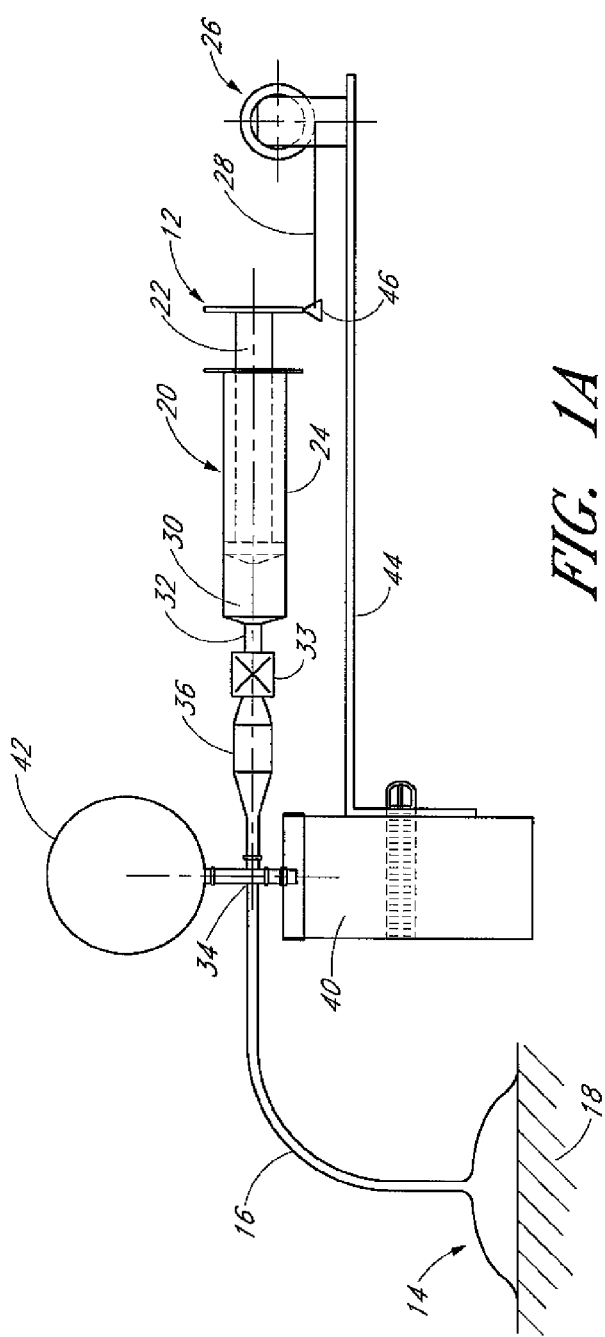
FIG. 1A is a schematic representation of the side of an embodiment, of a topical negative pressure therapy system.
FIG. 1B is a schematic representation of the end of an embodiment of a spring unit that can be used with the embodiments of the topical negative pressure therapy system illustrated in FIG. 1A.

The following detailed description is now directed to certain specific embodiments of the disclosure. In this description, reference is made to the drawings wherein like parts are designated with like numerals throughout the description and the drawings. It is to be noted that any of the features, components, configurations, sizes, materials, or any other details set forth in this disclosure with regard to particular embodiments are meant to also be combinable or substitutable with the components, features, or other details of any other embodiment disclosed herein where such a combination or substitution of such components, features, or other details is suitable.

Preferred embodiments described herein relate to wound therapy. The term "wound" as used herein, in addition to having its broad ordinary meaning, includes any body part of a patient that can be treated using reduced pressure. Wounds include, but are not limited to, open wounds, pressure sores, ulcers and burns. Treatment of such wounds can be performed using negative pressure wound therapy, wherein a reduced or negative pressure can be applied to the wound to facilitate and promote healing of the wound. Additional descriptions of devices, methods, and systems that can be used for wound therapy (e.g., for aspiration, irrigation, and cleansing of wounds) can be found in international patent application publication Nos. WO 2004/037334 (titled "APPARATUS FOR ASPIRATING, IRRIGATING AND CLEANSING WOUNDS"), WO 2005/046760 (titled "WOUND CLEANSING APPARATUS WITH HEAT"), and WO 2005/105180 (titled "APPARATUS FOR ASPIRATING, IRRIGATING AND/OR CLEANSING WOUNDS"), the entirety of each of which is hereby incorporated by reference as if fully set forth herein. It will also be appreciated that the negative pressure systems and methods as described herein can be applied to other parts of the body, and are not necessarily limited to treatment of wounds.

The apparatus and methods disclosed herein involve covering of the wound site with a dressing which can be configured to be sealed to the skin surrounding the wound by a flexible membrane type material through which or sealed thereto are conduits or tubes that can carry fluids to the wound site and/or away from the wound site. The fluids can be liquids such as wound exudates and/or irrigation or cleansing fluids such as saline, for example, but can also be gases such as air, for example, used to aerate the wound site and to assist the liquid fluids away from the wound site by aspiration means.

The above-referenced patent application publications WO 2004/037334, WO 2005/046760, and WO 2005/105180 describe systems for treating wounds by therapy usually involving a plurality of conduits needing to be sealed in respect of the dressing/wound site in order to prevent ingress of ambient atmosphere into the wound site and to enable the apparatus to work effectively and efficiently without significant leakage. Other embodiments of apparatuses are disclosed herein which apply topical negative pressure therapy to a wound having only one conduit or tube passing into the wound site.

As mentioned, there is a need for simple and inexpensive topical negative pressure therapy systems in, for example, third world countries and also for use by patients who wish to be mobile to continue daytime occupations while continuing beneficial topical negative pressure therapy. In some embodiments, a device can be provided that mitigates some of the disadvantages of known systems of reduced pressure generation.

Thus, according to some embodiments of the present disclosure, there is provided a system for the application of topical negative pressure therapy to a site on the body of a mammal (which can be a wound or otherwise), the system comprising a piston and cylinder device having a self-contained power source for the generation of a reduced pressure and for aspirating the site. In some embodiments, a dressing can be provided therewith, the dressing configured to cover the site and configured to be connectable to the piston and cylinder device by an aspirant conduit means, such as but not limited to an aspirant conduit or tube. In this arrangement, reduced pressure can be supplied to the dressing and, hence, the site. The dressing can be configured to sealingly surround the site.

In some embodiments, the device for generating a reduced pressure can be a syringe-type device having a cylinder and a slideable piston therein. The device can be configured to operate without a source of A/C power. In some embodiments, so as to be useable by a patient outside of conventional medical facilities such as a hospital or a convalescent bed, for example, the device can have its own power source. The power source can be a conventional battery, for example, powering a conventional DC electric motor driven pump. But, even these configurations can be heavier than desired, and the need to replace or recharge the batteries can be a disadvantage in terms of financial and infrastructural resources. Again, such systems can be relatively costly and also relatively inconvenient in terms of portability and continued power supply.

In some embodiments of the topical negative pressure generating device, the power source can be a mechanically generated motive source driving a simple suction generating unit such as a syringe-type unit, for example. Syringes are commonly available virtually everywhere in the world and are cheap and disposable. Syringes generally comprise a cylinder and an axially slideable piston and are available in a wide range of different sizes. The motive power for moving the piston in the cylinder in one embodiment according to the present disclosure can be a self-contained resilient member such as spring unit, for example. Suitable spring units include, but are not limited to, coiled ribbon springs which are available in many sizes to apply a wide range of forces. Such spring units can effectively apply a constant tension to the piston/piston rod of a syringe. Such a power source can be configured to be lightweight, inexpensive, compact, and portable. The simplicity of the device means it can be operated easily by any patient or clinician with a minimum of training.

Some embodiments of the device can also be provided with suitable features related to pressure measuring means, such as, but not limited to, mechanical or electronic sensors configured to display or reveal the pressure within the dressing and/or syringe cylinder. Some other examples of suitable pressure measuring devices which can be employed include, without limitation, purely pneumatic gauges or electronic gauges such as digital units, perhaps having their own battery power supply.

Some embodiments of the device can also be provided with suitable valve arrangements to ensure that fluid flows are in the correct directions (i.e., so as to prevent air or fluid flow into the dressing) when generating a reduced pressure, and suitable valve arrangements to ensure that reduced pressures are maintained in the dressing. In some embodiments, the valve can be configured such that one or more suction devices (such as, without limitation, a hand pump, suction bulb, a motorized pump, a battery powered pump, a piston, and syringe device, or any other suitable suction devices) can be connected and/or disconnected from the valve without the loss of pressure in the dressing.

Although wound exudates can be received directly into the pressure reducing syringe device and expelled therefrom when full into a suitable receptacle or waste disposal system in the case of relatively small wounds, a wound exudate fluid waste collecting receptacle to receive the aspirated exudate fluid from a wound site can be provided as part of the apparatus system in the case of larger wounds, for example. Suitable support means to support and accommodate the various features of the system devices can also be provided.

Additionally, in some embodiments, the system can comprise a manually operated suction device for evacuation of a wound/incision to apply topical negative pressure to the wound and can be used with any dressing design known in the art of topical negative pressure. The device can differ from other spring activated (kinetic devices) in, that it can be configured to provide a substantially constant level of pressure throughout the travel range of the piston in the cylinder. This is in contrast to known systems where a significant fall-off in pressure can be measured along the length of travel of a piston or bellows system or in the case of pre-evacuated accumulator bottles or manual pump/reservoir systems where the pressure constantly diminishes as the system or reservoir fills with fluid. Where a syringe-type pressure reducing device is used, the reduced pressure delivered can be controlled by choosing a different size of the syringe. For example, without limitation, the reduced pressure delivered can be controlled by varying the diameter of the syringe cylinder that is appropriate to the type of wound and wound volume. Additionally, without limitation, the reduced pressure delivered can be controlled by varying the size of and/or number of springs used to provide the force on the syringe.

In the system according to certain embodiments, the pressure or rate of pressure change generated can simply be controlled by using an appropriately sized syringe, i.e. by choosing a syringe with a different sized diameter, or changing the size/force of the spring unit.

In some embodiments, one spring can be used. In some embodiments, two or more springs can be used. Some embodiments of the device can be adapted so as to receive and support any number of interchangeable springs a range of tensions.

References in this disclosure to pressure "fall-off" or "diminishing" refer to the pressure difference between ambient atmospheric pressure and the reduced pressure pertaining in the dressing at the wound site. Therefore a reference to the pressure "diminishing" or "falling off" or other similar terms is meant to refer to the circumstance where the vacuum in the dressing is actually decaying and the pressure is rising towards that of ambient atmospheric pressure.

In a modification of the device, the syringe device and spring piston withdrawal unit can be arranged to be disconnectable from the system and replaceable by a hand-held pump to quickly reduce the pressure to a desired level. The connection between the pump/syringe motive source can be a one-way valve such as a non-return check valve, for example. Thus, the syringe unit can be removed, the hand pump attached, the system quickly pumped down, the hand pump removed and the syringe unit re-attached so as to maintain the desired reduced pressure. In some embodiments, a hand pump can be a bellows type hand pump, a suction bulb type pump, or any other suitable pump, and can have some or all of the characteristics of the embodiments of any of the pumps described herein.

In some embodiments, the hand pump and the syringe system can be supported by the apparatus and arranged in parallel such that the hand pump and the syringe system can be operated individually or simultaneously. In this arrangement, for example, the hand pump can be used to provide an initial drawdown of pressure in the dressing. Additionally, during operation, the pressure provided by the syringe can be augmented by operating the hand pump.

Additionally, in some embodiments, multiple syringe and piston units can be supported by the apparatus and arranged in parallel (either with or without the hand pump described herein) so that each of the multiple syringe and piston units can individually or simultaneously provide reduced pressure to the dressing. For example, in some embodiments, the apparatus or system can be configured such that two or more syringe and piston devices are arranged in parallel such that all of the piston and syringe devices can be in fluid communication with the dressing, depending on the valve arrangement or settings. In this configuration, each of the syringe and piston devices can be individually attached to one or more springs so that, as one syringe and piston device becomes filled with exudate or has otherwise reached its capacity, another of the syringe and piston devices can be activated so as to continue to provide reduced pressure to the wound dressing. If increased pressure drawdown to the dressing is desired, more than one of the syringe devices can be spring activated.

Additionally, the apparatus can have a valve or valve that permits any configuration or combination of the syringe devices or the hand pump device to be placed in fluid communication with the dressing. For example, in some embodiments having just a hand pump and a single syringe device, the valve can be configured to allow either the hand pump or the syringe device to individually be in fluid communication with the dressing, or to allow both the hand pump and the syringe device to be simultaneously in fluid communication with the dressing.

In particular, FIG. 1A is a schematic representation of the side of an embodiment of a topical negative pressure therapy system 10. FIG. 1B is a schematic representation of the end of an embodiment of a spring unit 26 that can be used with the embodiments of the topical negative pressure therapy system 10 illustrated in FIG. 1A.

The system 10 can comprise a device 12 for generating a reduced pressure operably connected to a dressing 14 via a conduit 16. The dressing can have any of the features or components of any of the dressings disclosed herein, or of any of the dressings known in the art or suitable for the application of reduced pressure. As illustrated, the dressing 14 is applied to a wound site 18. The device 12 can include a syringe 20 having a slideable piston/piston rod 22 moving in a stationary cylinder 24, the piston/piston rod 22 being connected to the constant tension spring units 26 each having a coiled ribbon spring 28.

In the illustrated embodiment, a spring unit 26 can comprise two or more individual constant tension spring units 26, two being shown. As the piston 22 is withdrawn from the cylinder 24 by the spring units 26, a volume 30 in the syringe 20 is increased. A tubular spigot 32 on the end of the cylinder 24 can be connected to a four-way union 34 via a vacuum check valve 36 which can allow fluid flow in only the left to right direction as viewed in FIG. 1A. A second port of the 4-way union 34 can be connected to a waste fluid reservoir 40 configured to receive waste exudate from the wound site 18 via the flexible plastics material conduit 16 operably connected at one end to the dressing 14 and at the other end to a third port in the 4-way union 34. A vacuum pressure gauge 42 can be connected to the fourth port of the 4-way union. The spring unit 26, syringe cylinder 24 and waste reservoir 40 can all be firmly held by a base plate 44 such that they are held substantially immobile relative to each other. The end of the piston/piston rod 22 can be connected to the ends of the ribbon springs 28 by a quick connect/disconnect clip 46.

In use, the spring unit 26 can be initially disconnected from the piston/piston rod 22 and the piston 22 traversed several times in the cylinder 24 so as to quickly reduce the pressure in the dressing 14, wound site 18, and/or the waste reservoir 40 to a desired level which can be confirmed by the gauge 42. In order to perform this initial evacuation of the dressing 14 and wound site 18, a manually or automatically openable and closable exhaust valve 33 can be positioned between the syringe tubular spigot 32 and one-way valve 36 so that the syringe 20 does not need to be disconnected to expel air at every stroke. Such a valve 33 can be a non-return valve configured to vent fluid to the atmosphere on a forward stroke to minimize volume in the cylinder 24. The piston/piston rod 22 can then be reconnected to the spring unit 26 by the clip 46, while the ribbon springs 28 are withdrawn from the spring unit 26 and the piston 22 is at the extreme left-hand end of its travel, i.e. the syringe 20 is emptied. A constant spring force can then be automatically applied to the piston/piston rod 22 by the spring unit 26 to withdraw it slowly in the rightwards direction. As exudate fluid is removed from the wound and/or leakage of air occurs into the system, the piston 22 can move slowly rightwards (when oriented as in FIG. 1A), maintaining the reduced pressure in the system. The reduced constant pressure is a function of the spring force and the area of the piston/cylinder of the syringe unit 20. As fluid is drawn from the wound site 18 through the conduit 16, the fluid can reach the 4-way union and can be drawn into the waste reservoir 40. As mentioned above, multiple syringe systems devices 12 and multiple spring systems 26 can be supported by the apparatus and used in fluid communication with the dressing 14.

Figure 2:
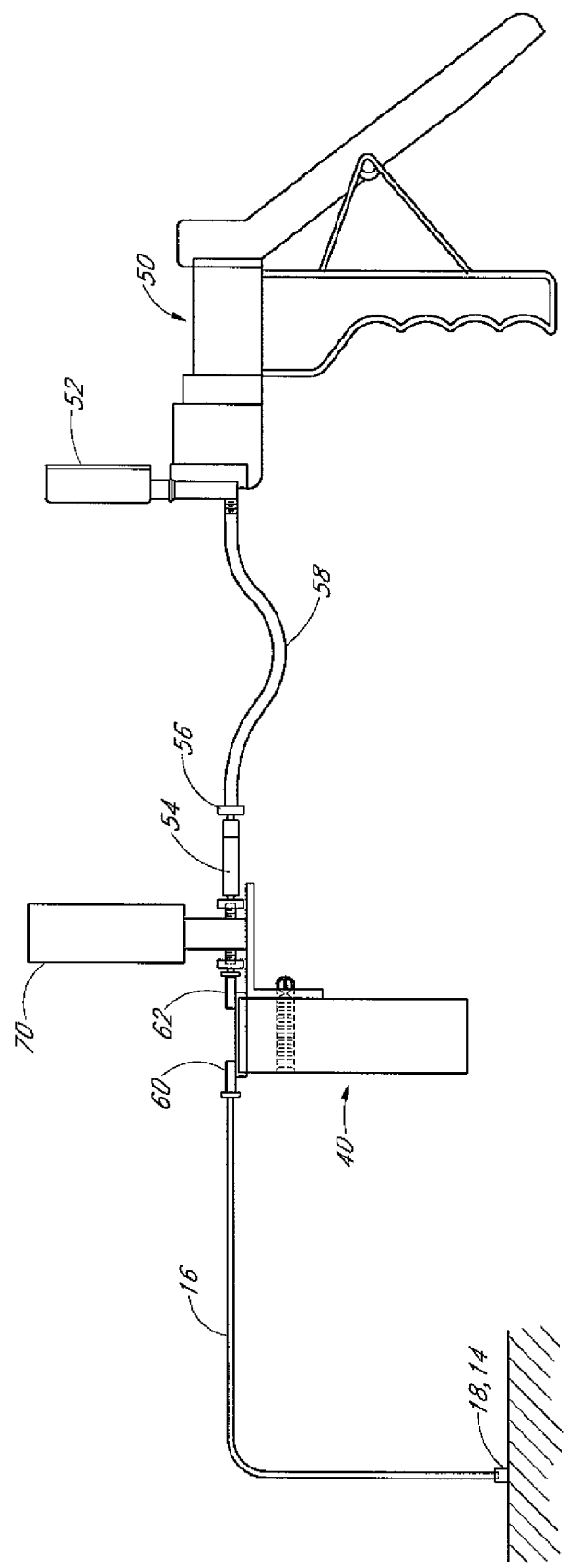
FIG. 2 is a schematic representation of the side of another embodiment of a topical negative pressure therapy system.

FIG. 2 is a schematic representation of the side of another embodiment of a topical negative pressure therapy system. The system illustrated in FIG. 2 is a modified version of the system shown in FIG. 1 and is intended for quickly creating a reduced pressure at the wound/dressing 18, 14. In this embodiment, a hand operated pump 50 is provided, some embodiments of which can have an integral pressure gauge

52. Although a hand operated pump is illustrated in FIG. 2, other pumps can be used as well, such as portable pumps including bulb pumps and portable battery powered pumps.

The pump 50 can be initially connected to a non-return one-way flow check valve 54 by means of a tapered threaded adapter 56 being a part of a connecting flexible conduit 58 between the pump 50 and check valve 54. The pump 50 can be configured to quickly reduce the pressure at the wound/dressing 18, 14 to a desired level. Once the desired pressure level is achieved, the pump 50 and conduit 58 can be disconnected from the valve 54, which can prevent or inhibit ingress of air into the dressing due to the valve 54 being a one-way valve. A pumping unit based upon the syringe 20 and constant tension spring unit 26 construction depicted in FIG. 1 can then be connected to the check valve 54 so that the desired pressure level can be automatically maintained. The pumping unit can also comprise a support to hold the cylinder 24 and spring unit 26 in fixed relationship and furthermore can be connected to the check valve 54 by a similar flexible conduit (not shown) to the flexible conduit 58 of the hand pump 50.

In some embodiments, the waste reservoir 40 can be similar or different as compared, to the waste reservoir 40 described above and illustrated in FIG. 1 in that the waste reservoir 40 illustrated in FIG. 2 can have an inlet port 60 connected to the conduit 16 to allow waste exudate from the wound to be captured in the waste reservoir 40 and an outlet port 62 connected to either the hand pump 50 and/or to the aspirating syringe 20, depending on what configuration is used. The outlet port 62 can be provided with a suitable filter (not shown) such as a pathogen filter of suitable pore size to prevent liquid exudate from passing out of the port 62 and also to prevent potentially bio-hazardous bacteria from eventually passing into the atmosphere.

In a further modification of the system of FIG. 2, an electronic pressure gauge 70 can be provided, which can have its own battery power supply. Some embodiments of the apparatus shown in FIG. 2 can also be optionally fitted with an audible alarm to warn the user if the pressure has deteriorated too far from a set point and the spring needs re-energizing.

A problem with conventional types of dressing is that they generally adhere to the patient's skin in order to form a seal therewith so as to form a sealed site to which topical negative pressure therapy can be applied. Generally, such dressings may need changing every day and in some cases much more frequently. In order to inspect a wound site for progress in healing, conventional dressings generally need to be removed and then a fresh dressing applied. Due to the adhesive nature of the dressing drapes commonly used, this can cause additional trauma to the patient by frequent removal of the dressing for whatever reason. Embodiments of the present disclosure are intended to mitigate some of the disadvantages of known systems of reduced pressure dressings.

In some embodiments, the dressing can comprise materials, aspects, and configurations of other topical negative pressure dressings known in the art, arranged or modified as described herein. Some embodiments of the dressings disclosed herein can comprise a thin, flexible sheet or membrane (also referred to herein as an overlay portion) to cover the wound, as is described in greater detail below. Some arrangements of the dressing can have an aspiration conduit sealingly supported by the flexible sheet or membrane.

Some arrangements of the dressing can comprise at least two parts: a first adherent base portion to sealably surround a wound site, for example, and a second detachable portion sealably connectable and reconnectable to said first portion to seal site. The second detachable portion can be configured to completely cover and, hence, provide a seal when joined with the base portion. Alternatively, the detachable portion can be configured to have an aperture formed therein so as to not provide a complete seal when joined with the base portion. In this arrangement, as will be described in greater detail below, a thin, flexible sheet can be provided that is positioned and sealingly sandwiched between the base portion and the second detachable portion. A benefit of the separate flexible sheet is that the sheet can be changed at regular intervals or as necessary so that any bacteria that has contaminated the flexible sheet can be discarded with the sheet and, hence, removed from the vicinity of the wound without requiring other components of the dressing to be discarded.

Thus, in some arrangements, the base portion can be formed being a generally ring-like shape having a circular or non-circular perimeter or shape. For example, without limitation, the base portion can have a square, rectangular, circular, ovular, polygonal, or any other suitable shape. Additionally, the lower surface of the base portion can be planar or non-planner, depending on the contour or surface shape of the skin or other surface against which the base portion would be adhered or sealed. Because the base portion in some embodiments is configured to surround the wound, the base portion can, be configured to define an aperture therethrough that is sufficiently large so that the base portion only contacts the healthy skin surrounding a wound.

As mentioned, some embodiments of the second detachable part can have a general shape that is similar to the shape of the base portion so that the tube can be joined together without any mismatch therebetween. However, because the base portion and the detachable portion are configured to be sealingly joined, the geometry of the base portion and the detachable portion pertaining to the sealing components can be different. For example, in some embodiments, the base portion can define an annular protrusion or tongue, as it is commonly referred, while the detachable portion can define an annular channel or groove configured to provide a seal when joined with the annular protrusion or tongue of the base portion. In this and other configurations, therefore, the second or detachable portion of the dressing can be detached from the first or base portion of the dressing so that the raised portion of the dressing can remain in place, adhered to the patient's skin. Additionally, the detachable portion and/or flexible sheet described above can be replaceable so that, if either of these components are contaminated such as by bacteria, they can be replaced with new, fresh components or can be cleaned or otherwise decontaminated without disturbing the wound and also without incurring the cost and time required to replace the base portion, and without causing irritation to the patient's healthy skin.

Thus, it will be seen that the first on base portion can be configured to remain in place around the wound, and tests have shown that it is feasible for the first part of the dressing to remain in place for up to a week. Additionally, in the same arrangements, the second or detachable portion can be removed by a clinician for inspection of the wound, changing or replacing of the gauze, foam, or other wound packing means within the dressing, cleansing of the wound, cleansing of the removable portions of the dressing, or for any other suitable purpose. The detachable portion can then be re-joined with the base portion without disturbing the seal between the base portion and the skin surrounding the wound. The detachable second portion need not have any adhesive on it which contacts the wound area per se.

As mentioned, the wound cavity can be provided with any suitable wound filling material known in the art. In some applications, the wound filling material can be configured to maintain the edges of the wound cavity apart from one another and to promote the growth of new material from the wound bed so as to prevent the formation of closed cavities. The embodiments of the dressing disclosed herein facilitate the use of wound filler materials by allowing any internal wound fillers, wound packing materials, or waste absorbing materials to be easily accessed by removing the second detachable portion of the dressing without disturbing the seal between the lower base portion and the patient's skin.

In arrangements where the dressing comprises a flexible sheet sandwiched between the base and the detachable portion of the dressing, the flexible sheet can provide the advantage of being able to collapse over and cover a wound filler that can be placed within the dressing. In some embodiments, the flexible sheet can be configured to cover a wound filler that protrudes above the edge of the detachable portion of the dressing in a manner that may not be achievable with a more rigid wound dressing.

In some of the embodiments described herein, because the volume or capacity of the exudate waste collecting receptacle can be limited or relatively small, the gauze or wound packing material can be selected so that the apparatuses described above can have additional means for collecting waste fluid. Providing additional means for collecting waste fluid can extend the time periods between which the waste receptacle needs to be emptied or replaced. This may be particularly useful in applications where the topical negative pressure therapy system is used as a portable system to allow patients to lead a relatively normal life while continuing their therapy (though in theory the waste receptacle could be as large as desired).

Thus, in some embodiments, the wound packing material may comprise a so-called "superabsorber" material to absorb excess waste fluids which would otherwise be aspirated to the waste receptacle. In some embodiments, between approximately 50% and approximately 100% of the fluids exuded by the wound can be absorbed by the superabsorber with the remaining portion of the fluids exuded by the wound can be aspirated to the waste receptacle or otherwise. A suitable material for a superabsorber can be polyacrylate (in particle form or otherwise), calcium alginate, and/or carboxymethycellulose.

In some embodiments, the superabsorber can be held within a porous or permeable bag within the dressing, and can be positioned adjacent the wound. In some embodiments, the wound packing material can be a composite containing the superabsorber material, such as gauze with superabsorber particles or fibers contained therein, or a foam material such as ALLEVYN PLUS™ having polyacrylate superabsorber particles therein. In some embodiments, the superabsorber material can be positioned or layered on top of a porous foam material or other suitable material so that exudate travels through the foam or other material before being absorbed by the superabsorber material. This arrangement would allow a user or medical practitioner to easily and quickly change the superabsorber material with or without changing the other wound packing materials.

Consequently, it will be seen that some embodiments of the dressing system disclosed herein can have at least two advantages. First, some embodiments of this dressing can result in reduced trauma to the patient since the base part can remain in sealing contact on the patient for much longer than with conventional topical negative pressure dressings. Additionally, the base portion can be configured so as to reduce the area of contact with the patient's skin. Furthermore, the second detachable portion need have no adhesive which contacts either sound skin or the wound itself, again leading to reduced trauma for the patient.

In the case where the wound site comprises a skin graft or skin replacement product, for example, which often are secured with minimal suture material, topical negative pressure can be used to apply a moderate pressure via a positive pressure from the ambient atmosphere to the graft to stabilise the graft and assist with complete contact over the graft area. The use of topical negative pressure in skin graft surgery also helps to prevent the graft from being continuously wet by removing any excess fluids via the aspiration conduit. The fact that the second portion may have no adhesive thereon, in contrast to conventional self-adhesive drape materials, can reduce the danger of possibly harming a delicate bond of the graft to the wound site.

The first base portion of the dressing may be provided with a conventional type of multi-layer construction to both protect adhesive coated surfaces with a removable and discardable protector layer and a support layer to assist handling of the dressing portion immediately prior to adhering to a patient. If provided with an adhesive layer, the second portion can also be provided with similar protective and support layers.

In some embodiments, however, the second or removable portion can be provided with an adhesive layer to adhere the first and second portions of the dressing together. There can be particular applications where this arrangement is preferred. Other arrangements of the dressing, as described herein, can be configured such that the base portion and the detachable portion are provided with mutually co-operating joining and sealing means.

Mutually co-operating sealing means may, in some embodiments of the present disclosure, comprise co-operating ring portions on the two parts which have engaging male and female portions (in cross section) formed from a soft, conformable material such as but not limited to a silicone rubber type material, polyurethane, PE, PP, PVC, EVA, for example. Suitable materials can have a Shore A hardness in the range from about 70 to about 100, but this range is not limiting.

Therefore, in some arrangements of the dressing, the second portion can be configured so that it forms a seal enclosure over the first base portion. For example, a second portion can be configured such that a flexible drain or window portion (whether translucent, transparent, or otherwise) can be integral or otherwise adhered to the second portion. Alternatively, some arrangements of the dressing can be configured such that a separate drape or flexible film material (such as can be formed from, without limitation, a translucent, transparent, opaque plastic material or any other suitable material) but which can be held in place by being sandwiched between the male and female co-operating portions of the base and detachable portions. Although co-operating male and female formations or features are described above for joining the base portion and the second detachable portion, alternative joining means such as magnetic material filled tapes, for example, can be used.

Figure 3A:
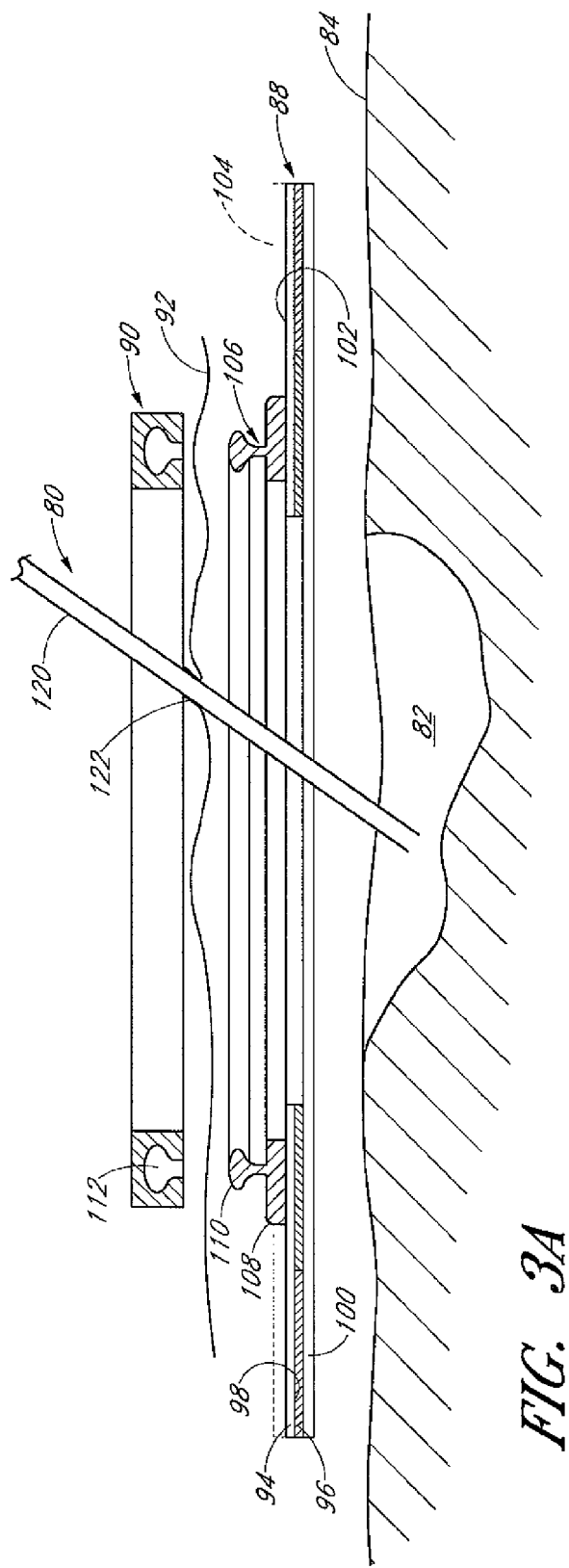
FIG. 3A is an exploded sectional view through the center of an embodiment of a dressing that can be used in a topical negative pressure therapy system.
Figure 3B:
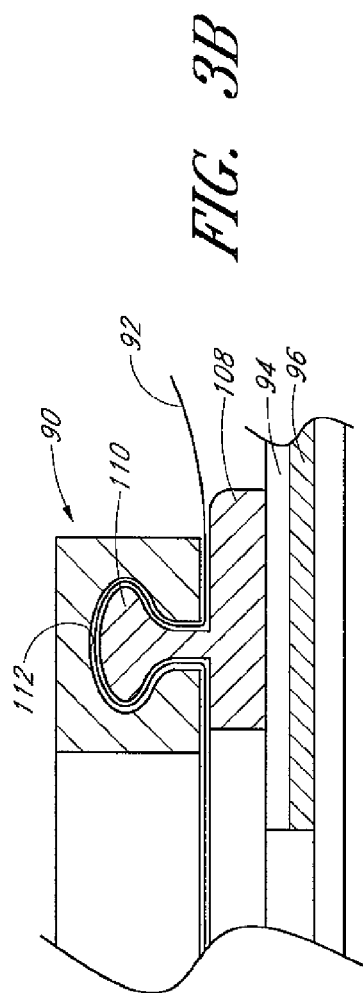
FIG. 3B is a sectional view through the center of the embodiment of the dressing shown in FIG. 3A showing a portion of the embodiment of the dressing in an assembled state.

In particular, with reference to the accompanying figures, FIG. 3A is an exploded sectional view through the center of an embodiment of a dressing that can be used in a topical negative pressure therapy system, and FIG. 3B is a sectional view through the center of the embodiment of the dressing shown in FIG. 3A, showing a portion of the embodiment of the dressing in an assembled state.

The embodiment of the dressing 80 illustrated in FIGS. 3A and 3B can be used in the system illustrated in FIGS. 1A, 1B, and/or 2. As mentioned, FIG. 3A shows the dressing 80 in exploded form showing the constituent parts situated above a schematic wound 82 surrounded by healthy skin 84, and FIG. 3B shows a detail of the first base portion 88, the second detachable portion 90, and the occlusive drape material or membrane 92 all joined together with the membrane 92 sandwiched between the first base portion 88 and the second detachable portion 90. The dressing can comprise a first base portion 88 and a second detachable portion 90. In this embodiment, the second detachable portion 90 can be in the form of a ring member which can be removably attached to the base portion 88 by co-operating male and female engagement features described below. In some embodiments, the membrane 92 can be a separate component formed from a thin, flexible material and can, be provided between the first base portion 88 and second detachable portion 90. In some embodiments, as described above, the detachable portion 90 can be configured to completely cover the base portion 88 and hence, the wound 82. In some embodiments, the membrane 92 can be integrally formed with the detachable portion 90, or can be separately formed and adhered or otherwise fixed to the detachable portion.

In some embodiments, the detachable portion 90 can be hingedly connected or otherwise tethered to the base portion 88. In some embodiments, the detachable portion 90 can be untethered from the base portion 88, so that the detachable portion 90 can be completely removed from the base portion 88.

Prior to attachment to the skin 84, the first base portion 88 can comprise a flexible plastic material backing layer 94 having a layer of pressure sensitive adhesive 96 coated on the surface 98 which is configured to contact the skin in use. The adhesive layer 96 can be initially protected by a plastic material protective layer 100 which can be peeled away prior to adhering to the patient. Depending upon the size and physical stiffness of the carrier layer 94, a further removable adhesive stiffening carrier layer (shown as dashed lines 104 in FIG. 3) can optionally be provided upon the upper surface 102 of the backing layer 94 to aid handling of the first base portion 88 after removal of the adhesive protection layer 100. The carrier layer 104 can be peeled away after attachment of the first base portion 88 to the patient. The first base portion 88 can also be provided with a connector ring 106 adhered thereto. The first base portion 88 and any other suitable component of the dressing 80 can be formed from a soft conformable material such as, but not limited to, a plastic or rubber material such as a silicone rubber or other materials as described hereinabove. The connector ring 106 can have a foot portion 108 for greater bonding strength and stability and an upstanding male engaging portion 110 molded therewith.

The second detachable portion 90 can be a ring member of corresponding size to that of connector ring member 106 and can be provided with a female engaging portion 112 to cooperate with and receive the male portion 110 of the connecting ring 106 therein. In some embodiments, the interconnection of the male and female engaging portions 110, 112 can create an airtight or approximately airtight seal. The second ring member 90 and any other suitable component of the dressing 80 can be molded from a soft conformable plastic material such that forces to join the first base portion 88 and the second detachable portion 90 are relatively low, so as to avoid trauma to the patient. Any components of the dressing 80 can be sized and shaped, so as to accommodate a wide range of wound sizes and body surface contours.

Some embodiments of the dressing can comprise an aspirant conduit configured to allow a source of reduced pressure to be applied to the volume beneath the dressing. In some embodiments, the aspirant conduit can be incorporated into the dressing by providing separate, occlusive drape portions having one or more aspirant tubes sealed thereto ready for installation in a dressing. The drape portion can be configured to be removably sandwiched between the base portion and the detachable portion, or can be configured to be integrally formed with or otherwise fixed to the second detachable portion of the dressing. This can be advantageous where a separate occlusive drape portion can be employed having no adhesive coating layer.

Some embodiments of the aspirant coolant can comprise a valve or connector configured to receive and mate with a length of tubing from, for example, the source or reduced pressure. The aspirant conduit means can be formed as an integral part of the first base dressing portion during manufacture having a flexible, overlong conduit which can be cut to a desired length, both internally and externally of the dressing site, during application of the dressing to the wound site.

Alternatively, in some embodiments, the base first portion can have a tubular spigot molded or otherwise incorporated therewith and to which an aspirant conduit can be connected. Such a spigot can have a portion of the aspirant conduit connected internally of the dressing and can have an additional portion of aspirant tube to connect to aspirating pump means after placement of the dressing on a patient.

With reference to FIGS. 3A and 3B, an aspirant conduit 120 can be incorporated in several ways into the dressing 80. In addition to the ways described above, as shown in FIG. 3A, a conduit 120 can be passed through the drape 92 and sealed thereto at points of contact 122. This can be achieved by providing occlusive drape portions having aspirant tubes sealed thereto and configured to be ready for installation in a dressing as described. Additionally, the base portion 88 can have an aperture formed therein, the aperture being configured to receive and allow a conduit to pass therethrough. The aperture can be configured so that, as the conduit is passed therethrough, a sufficient seal can be formed between the aperture and the conduit. In some embodiments, an adhesive or suitable sealing material can be applied to seal the outside surface of the conduit with the aperture.

Generally, conduits or tubes passing into the wound site in any of the embodiments described herein can be sealed to a flexible wound covering membrane or film by "pinching" the flexible covering around the conduit or tube so as to both stick the membrane material to the conduit or tube and also to itself to form a seal with the tube. Generally, the types of flexible membrane material used for wound coverings are provided with an adhesive layer such as a pressure sensitive adhesive, for example, in order for the material to adhere to the skin surrounding a wound.

In some embodiments, a conduit insertion device having a trocar supported therein can be used to pass the conduit through either the flexible sheet or the second detachable portion after the dressing has been positioned over the wound. Some arrangements of the conduit insertion device can be configured such that, after the conduit has been passed through the flexible sheet or the second detachable portion (if the flexible sheet is not use), a tabbed or flanged surface that can be formed on a portion of the conduit can be sealably adhered or otherwise attached to the outside surface of the flexible sheet or second detachable portion to secure the conduit thereto.

For example, in some embodiments, a trocar can be supported within the tubular length of conduit that can be inserted though the dressing such that the trocar protrudes past the distal end of the conduit (i.e., the end of the conduit to be positioned within the dressing). In this configuration, the trocar can be used to create a puncture hole in the flexible sheet, the second detachable portion of the dressing, and/or the base portion of the dressing to permit the tubing to pass therethrough. After the tubing has been passed therethrough, the conduit member may be advanced to a distance that is sufficient to permit an annular tabbed or flanged surface sealingly surrounding the tubing to be attached to, adhered to, or otherwise joined with the outside surface of the dressing so that an approximately hermetic seal is formed between the conduit member and the dressing. At that point, the trocar may be withdrawn and the proximal end of the tubing (i.e., the end of the tubing that is located outside of the dressing), may be connected directly or indirectly to the supply of reduced pressure.

Throughout the description and claims of this specification, the words "have," "comprise," "contain," and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

While the above detailed description has shown, described, and pointed out novel features as applied to various embodiments, it will be understood that various omissions, substitutions, and changes in the form and details of the device or process illustrated can be made without departing from the spirit of the disclosure. Additionally, the various features and processes described above can be used independently of one another, or can be combined in various ways. All possible combinations and subcombinations are intended to fall within the scope of this disclosure.

As will be recognized, certain embodiments described herein can be embodied within a form that does not provide all of the features and benefits set forth herein, as some features can be used or practiced separately from others. The scope of the inventions is indicated by what is claimed in this and/or future applications rather than by the foregoing description. All changes which come within the meaning and range of equivalency of the claims in this and/or future applications are to be embraced within their scope.

What is claimed is:

1. A system for the application of negative pressure therapy, comprising:
    a pump for generating negative pressure;
    a dressing for covering and protecting a wound, the dressing comprising a porous layer configured to contact the wound, a cover layer, and an absorbent layer between the porous layer and the cover layer;
    a first conduit having a first end connected to the dressing and a second end extending away from the dressing;
    a second conduit having a first end configured to be connected to the pump and a second end configured to extend away from the pump, wherein the first and second conduits are configured to be fluidically connected to provide fluid communication between the pump and the dressing; and
    a one-way valve provided at the second end of the first conduit and configured to be in-line between the pump and the dressing when the first and second conduits are fluidically connected, wherein the second conduit is configured to be fluidically disconnected from the first conduit after negative pressure has been applied to the dressing from the pump and the one-way valve is configured to maintain a negative pressure within the dressing when the second conduit is disconnected.

2. The system of claim 1, wherein the second end of the second conduit is configured to be removably connected to the one-way valve.

3. The system of claim 1, wherein the pump comprises a portable battery powered pump.

4. The system of claim 1, wherein the one-way valve is integral with the first conduit.

5. The system of claim 1, wherein the absorbent layer comprises superabsorbent material.

6. The system of claim 1, wherein the absorbent layer comprises carbomethoxycellulose.

7. The system of claim 1, further comprising a second suction device configured to generate negative pressure within the dressing, the second suction device being removably connectable to the one-way valve.

8. A method for the application of negative pressure therapy to a wound, the method comprising:
    sealingly enclosing the wound with a dressing comprising a porous layer configured to contact the wound, a cover layer and an absorbent layer between the porous layer and the cover layer; wherein ambient air is substantially prevented from entering a space between the cover layer and the wound;
    operating a pump to apply a desired level of negative pressure within the dressing, wherein the pump is connected to the cover layer through a fluid passage so that the pump is in fluid communication with the space between the cover layer and the wound, and wherein the negative pressure is applied through a one-way valve in-line between the pump and the dressing, wherein the fluid passage comprises:
        a first conduit providing fluid communication between the dressing and the one-way valve and a second conduit providing fluid commination between the one-way valve and the pump; and
    disconnecting the second conduit from the first conduit, wherein the one-way valve maintains a negative pressure within the dressing when the second conduit is disconnected from the first conduit.

9. The method of claim 8, wherein the second conduit comprises a first end connected to the pump and a second end removably connected to the one-way valve when the pump is operated to apply the desired level of negative pressure.

10. The method of claim 8, wherein disconnecting the second conduit from the first conduit comprises disconnecting the second conduit from the one-way valve.

11. The method of claim 8, further comprising reconnecting the second conduit to the first conduit and re-operating the pump to apply negative pressure within the dressing.

\* \* \* \* \*

UNITED STATES PATENT AND TRADEMARK OFFICE
CERTIFICATE OF CORRECTION

| | |
|---|---|
| PATENT NO. | : 11,344,663 B2 |
| APPLICATION NO. | : 16/201508 |
| DATED | : May 31, 2022 |
| INVENTOR(S) | : Edward William Walton |

It is certified that error appears in the above-identified patent and that said Letters Patent is hereby corrected as shown below:

On the Title Page

On Page 6, Column 1, Line 12, Item (56) under Other Publications, delete "Reporton" and insert --Report on--.

In the Specification

In Column 1, Line 44, delete "wound," and insert --wound.--.

In Column 4, Line 53, delete "generation," and insert --generation--.

In Column 6, Line 5, delete "embodiment," and insert --embodiment--.

In Column 8, Line 23, delete "piston," and insert --piston--.

In Column 8, Line 40, delete "in," and insert --in--.

In Column 9, Line 50, before "that" insert --system--.

In Column 11, Line 23, delete "compared," and insert --compared--.

In Column 12, Line 28, delete "can," and insert --can--.

In Column 13, Line 47, delete "carboxymethycellulose." and insert --carboxymethylcellulose.--.

In Column 15, Line 19, delete "can," and insert --can--.

In Column 15, Line 30, delete "88," and insert --88.--.

In Column 17, Line 6, delete "though" and insert --through--.

Signed and Sealed this
Fourteenth Day of March, 2023

*Katherine Kelly Vidal*

Katherine Kelly Vidal
*Director of the United States Patent and Trademark Office*

CERTIFICATE OF CORRECTION (continued)
U.S. Pat. No. 11,344,663 B2

In the Claims

In Column 18, Claim 8, Line 53, delete "commination" and insert --communication--.